United States Patent [19]

Szantay et al.

[11] 4,173,642
[45] * Nov. 6, 1979

[54] VASODILATING 1,1-DI-(2-METHOXYCARBONYL-ETHYL)-1,2,3,4,5,6,12,12B-OCTAHYDRO-INDOLO[2,3-a]QUINOLIZINE

[75] Inventors: Csaba Szantay; Lajos Szabo; György Kalaus; Egon Karpati, all of Budapest; Laszlo Szporny, Szabolcska M u., all of Hungary

[73] Assignee: Richter Gedeon Vegyeszeti Gyár Rt, Budapest, Hungary

[*] Notice: The portion of the term of this patent subsequent to Nov. 8, 1994, has been disclaimed.

[21] Appl. No.: 865,428

[22] Filed: Dec. 29, 1977

[30] Foreign Application Priority Data

Dec. 30, 1976 [HU] Hungary ................. RI 612

[51] Int. Cl.² .................. C07D 471/04; A61K 31/445
[52] U.S. Cl. ....................... 424/267; 546/70
[58] Field of Search .................. 260/293.53, 293.55; 546/70; 424/267

[56] References Cited

U.S. PATENT DOCUMENTS

| | | | |
|---|---|---|---|
| 3,536,725 | 10/1970 | Schvt | 260/293.53 |
| 3,830,823 | 8/1974 | Castaigne | 260/293.53 |
| 4,033,969 | 7/1977 | Sevenet et al. | 260/293.53 |
| 4,057,551 | 11/1977 | Szantay et al. | 260/293.53 |
| 4,057,551 | 11/1977 | Szantay et al. | 546/70 |
| 4,089,856 | 5/1978 | Szantay et al. | 546/70 |

FOREIGN PATENT DOCUMENTS

| | | | |
|---|---|---|---|
| 2192107 | 2/1974 | France | 546/70 |
| 983848 | 2/1965 | United Kingdom | 260/293.53 |
| 1351262 | 4/1974 | United Kingdom | 546/70 |

OTHER PUBLICATIONS

Chemical Abstracts: 85:46624q, (1976) [Szantay et al., German Offen. 2,541,484, 4/15/76].
Imbert; T. et al., Bull. Soc. Chim. France, 1973 (No. 9-10), 2705-2709.

Primary Examiner—John M. Ford
Assistant Examiner—Richard A. Schwartz
Attorney, Agent, or Firm—Karl F. Ross

[57] ABSTRACT

New pharmacologically active octahydro-indolo[2,3-a]quinolizine derivatives of the formula

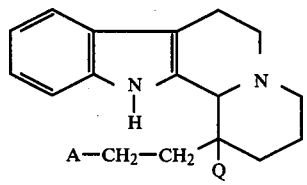

wherein Q is hydrogen or an A—CH₂—CH₂— group and A is cyano or -COOR, wherein R is $C_{1-6}$ alkyl are prepared by reacting 2,3,4,6,7,12-hexahydro-indolo[2,3-a]quinolizine with a compound of the formula CH₂=CH—A, and reducing the obtained hexahydroindolo[2,3-a]quinolizine derivative of the formula

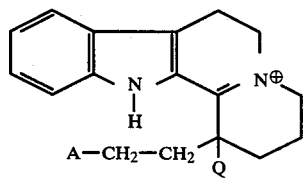

2 Claims, No Drawings

VASODILATING 1,1-DI-(2-METHOXYCARBONYL-ETHYL)-1,2,3,4,5,6,12,12B-OCTAHYDRO-INDOLO[2,3-a]QUINOLIZINE

The invention relates to pharmaceutically active new indoloquinolizine-monoesters, diesters or nitriles and pharmaceutical compositions containing the same.

The new octahydro-indolo[2,3-a]quinolizine derivatives according to the invention, which contain one or two cyanoethyl group(s) or one or two alkoxycarbonylethyl group(s) in position 1, correspond to the formulae

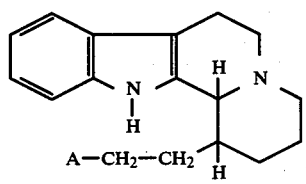

(XIaX)

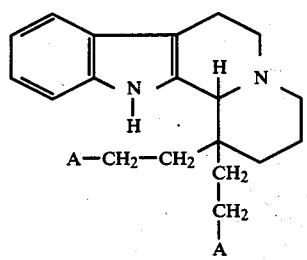

(XIbX)

wherein A represents a cyano group or a group of the formula —COOR, and R is a $C_{1-6}$ alkyl group. The pharmaceutically acceptable acid addition salts of the above compounds are also within the scope of the invention.

The alkyl group represented by symbol R is a straight-chain or branched $C_{1-6}$ alkyl group, such as methyl, ethyl, n-propyl, isopropyl, n-butyl, isobutyl, tert.-butyl, amyl, isoamyl, n-hexyl or isohexyl group.

The most preferred representatives of the compounds having the formula (Ia) are those wherein A represents a cyano group, a methoxycarbonyl group or an ethoxycarbonyl group. Of the compounds having the formula (Ib) the derivative wherein A is methoxycarbonyl group is most preferred. The pharmaceutically acceptable acid addition salts of the above compounds are equally preferred.

The compounds of the formulae (Ia) and (Ib) are asymmetric in structure; thus they can be resolved in a manner known per se to obtain the respective optically active compounds. Both the racemic and the optically active compounds of the formulae (Ia) and (Ib) are within the scope of the invention.

The compounds of the formulae (Ia) and (Ib) and the pharmaceutically acceptable acid addition salts thereof possess vasodilating effects and can be used in therapy in the form of pharmaceutical compositions.

Hexahydro intermediates of the formulae (IIa) and (IIb),

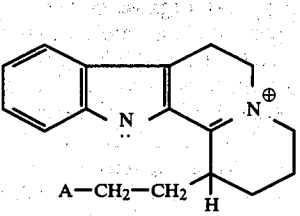

(XIIaX)

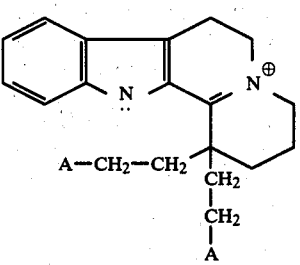

(XIIbX)

wherein A represents cyano group, have already been described in the U.S. Pat. No. 3,536,721. These compounds have no disclosed pharmaceutical effect. According to the process described in the cited reference the products obtained require chromatographic purification, thus yields exceeding 30% cannot be attained. By contrast, the known hexahydro intermediates of the formulae (IIa) and (IIb), wherein A is cyano group, can be prepared with a yield of 86% by this process of the invention. Those compounds of the formulae (IIa) and (IIb), wherein A is a —COOR group and R is a $C_{1-6}$ alkyl group, are novel substances.

The new compounds of the formulae (Ia) and (Ib), wherein A is cyano group or a group of the formula —COOR and R is a $C_{1-6}$ alkyl group, or the pharmaceutically acceptable acid addition salts of these compounds can be prepared according to this invention as follows: 2,3,4,6,7,12-hexahydro-indolo[2,3-a]quinolizine of the formula (III)

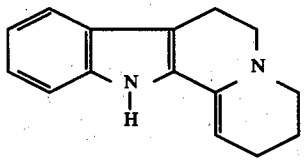

/III/ is reacted with a compound of the formula (IV),

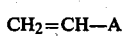

CH$_2$=CH—A  (IV)

wherein A is as defined above, the resulting compound of the formula (IIa) and/or (IIb) is, optionally after coverting it into an acid addition salt, reduced, the resulting compounds of the formulae (Ia) and (Ib), wherein A is as defined above, are optionally separated from each other, and, if desired, a thus-obtained ester is transesterified or a thus-obtained nitrile is converted into ester in a manner known per se, and, if desired, a compound of the formula (Ia) or (Ib), wherein A is as defined above, is converted into its pharmaceutically acceptable acid addition salt.

The starting substance of the formula (III) can be prepared as described in J. Heterocycl. Chem. 3, 101 (1966).

The formula (III) compound is reacted with a compound of the formula (IV), wherein A is as defined above, preferably in an inert organic solvent, e.g. a halogenated hydrocarbon, such as dichloromethane. When a compound of the formula (IV), wherein A is a group of the formula —COOR, is used as a reactant, the reaction is performed preferably in a mixture of an inert organic solvent as defined above and an alcohol of the formula R—OH, wherein R corresponds to substituent R of the reactant. The reaction temperature is not critical; it is preferred, however, to perform the reaction under mild conditions at room temperature. The reaction time is not critical, and it may vary between 0.5 and 3 days depending on the reaction temperature. The reaction can be performed optionally in an inert gas atmosphere, such as a nitrogen or an argon atmosphere.

The reaction mixture is processed in a manner known per se, e.g. by evaporating the solvent or solvent mixture and optionally removing the excess of the reactant of the formula (IV) by treating the residue with an appropriate solvent, such as petroleum ether. If desired, the resulting compound(s) of the formula(e) (IIa) and-/or (IIb), obtained most frequently as crystalline substances, can be converted into acid addition salts. The acid addition salts are prepared e.g. by dissolving the base in an inert organic solvent, preferably in an aliphatic alcohol, and adding the appropriate acid, to the resulting solution. As the acid preferably a mineral acid, such as a hydrogen halide or a perhaloacid (e.g. perchloric acid) is applied.

The compound(s) of the formula(e) (IIa) and/or (IIb) can be reduced with a chemical reducing agent or with catalytically activated hydrogen. In this step the free bases or the acid addition salts, or the pure mono- or disubstituted compounds or mixtures thereof can equally be used as starting substances.

The reducing agent and the reaction conditions are selected so that the indoloquinolisine ring is saturated without the simultaneous reduction of the cyano group optionally present.

When a chemical reducing agent is used in the reaction, it is preferable to use a complex metal hydride, particularly a borohydride, such as lithium, sodium or potassium borohydride.

The borohydride reduction is performed in the presence of a solvent or suspending agent inert to the reaction. As reaction medium preferably an aliphatic alcohol, such as methanol, or an aqueous alcohol, such as aqueous methanol, is used.

The borohydride is added to the reaction mixture in excess, preferably in a 1.5 to 7-fold molar excess. The reaction temperature and reaction time are not decisive factors; they depend primarily on the reactivities of the starting substances. The reaction is performed generally at a temperature of about 0° C., and the mixture is stirred for about 0.25 to 3 hours after admixing the reactants with each other.

When the reduction is performed with catalytically activated hydrogen, preferably a metal, such as palladium, platinum, nickel, iron, copper, cobalt, chromium, zinc, molybdenum, tungsten, etc., or an oxide or sulfide of such metals is used as a catalyst. Supported catalysts can be used as well, decreasing thereby the amount of expensive noble metal necessary for the reduction. As a support e.g. carbon (particularly charcoal), silicon dioxide, aluminum oxide or sulfates or carbonates of alkaline earth metals can be used.

When the reduction is performed with catalytically activated hydrogen, it is preferred to use palladium (particularly palladium-on-charcoal) or Raney-nickel as catalyst; the catalyst is selected, however, always by taking into account the properties of the substance to be reduced and the reaction conditions.

Catalytic hydrogenation is performed in a solvent inert towards the reaction, such as an alcohol, a halogenated hydrocarbon, ethyl acetate, glacial acetic acid, or mixtures thereof. Aliphatic alcohols, such as methanol and ethanol, as well as halogenated hydrocarbons, such as dichloromethane and dichloroethane, and mixtures of such solvents have proved to be particularly preferable. When platinum oxide is used as the catalyst, it is preferred to perform the reaction in a neutral or slightly acidic medium, whereas when Raney-nickel is the catalyst, preferably a neutral or alkaline medium is used.

The temperature, pressure and time of the catalytic reduction step may vary within wide limits depending on the starting substances. It is preferred, however, to perform the reaction at room temperature under atmospheric pressure until hydrogen uptake ceases. Hydrogen uptake ceases generally within a period of 10 minutes to 5 hours.

According to a preferred method of the invention the catalytic hydrogenation is performed so that the catalyst, preferably palladium-on-charcoal, is washed with water and the solvent used in the hydrogenation step, preferably methanol, then the catalyst is prehydrogenated, thereafter a solution of the starting substance [compound(s) of the formula(e) (IIa) and/or (IIb) or acid addition salts thereof] in the above solvent is admixed with the catalyst, and the mixture is hydrogenated preferably at room temperature and atmospheric pressure until the hydrogen uptake ceases.

When a mixture of the compounds of the formulae (Ia) and (Ib) is obtained in the reduction, the individual components can be separated from the mixture according to known techniques. One of these techniques is preparative layer chromatography; in this instance separation is based on the fact that the $R_f$ value of the disubstituted compound of the formula (Ib) is higher than that of the monosubstituted derivative of the formula (Ia).

As the adsorbent preferably silica gel Merck $PF_{254-366}$ is used. Various solvent mixtures can be used as eluting agent; mixtures of benzene and methanol, particularly a 14:2 mixture, are preferred [Halpaap, H.: Chemie-Ing.-Techn. 35, 488 (1963)].

The end-products of the formulae (Ia) and (Ib) were subjected to I.R. analysis. The Bohlmann bands appearing in the I.R. spectra of both compound types indicate that the hydrogen atoms in positions 12b and 1, furthermore the hydrogen atom in position 12b and the —CH$_2$—CH$_2$—A group in position 1 are of $\beta$ conformation, i.e. the compounds of the formulae (Ia) and (Ib) are of trans configuration.

Those compounds of the formula (Ia) or (Ib), wherein A is a —COOR group and R is $C_{1-6}$ alkyl, can be subjected to transesterification in a manner known per se. Thus if one of the esters has already been prepared, this compound can be converted easily into any desired other ester. Transesterification can be performed by boiling a compound of the formula (Ia) or (Ib), wherein A is a —COOR group and R is $C_{1-6}$ alkyl, in an alcohol corresponding to the new ester group to be introduced into the molecule in the presence of an alkali metal alcoholate, preferably sodium alcoholate, corresponding to this alcohol. If desired and possible, the alcohol liberated in the transesterification process, the boiling point of which is lower than that of the alcohol applied as solvent, is continuously removed from the mixture by distillation.

Those compounds of the formula (Ia) or (Ib), wherein A represents cyano group, can be converted into the respective esters, i.e. to compounds wherein A is a —COOR group and R is a $C_{1-6}$ alkyl group. In this instance one can proceed e.g. by boiling a compound of the formula (Ia) or (Ib), wherein A is cyano group, in a dilute aqueous solution of a mineral acid (such as hydrochloric or sulfuric acid) or of an inorganic base (such as sodium hydroxide, potassium hydroxide, etc.), and esterifying the resulting carboxylic acid in a manner known per se. In this latter step the carboxylic acid can be boiled in an alcohol corresponding to the ester group to be introduced into the molecule. According to another method the carboxylic acid is converted e.g. into its silver salt and this salt is reacted with an alkyl halide, preferably iodide, corresponding to substituent R to be introduced into the molecule. In a still further method the carboxylic acid is converted first into a reactive derivative, preferably an acid halide or anhydride, and the resulting reactive derivative is reacted with an alcohol of the general formula R—OH, wherein R is a $C_{1-6}$ alkyl group, corresponding to the R substituent to be introduced into the molecule. The cyano compounds can also be converted into esters by reacting them with an excess of an alcohol corresponding to the ester group to be introduced in the presence of hydrochloric acid; in this instance the desired ester is obtained through an iminoether derivative.

If desired, the compounds of the formulae (Ia) and (Ib), wherein A is as defined above, can be purified e.g. by recrystallization. As solvent e.g. aliphatic alcohols, such as methanol, ethanol or isopropanol, aliphatic ethers, such as diethyl ether, etc. can be used.

The compounds prepared according to the invention can also be purified by preparative layer chromatography. In this instance preferably silica gel Merck $PF_{254-366}$ is applied as adsorbent, and various solvent combinations, such as mixtures of benzene and methanol (preferably a 14:2 or 14:3 mixture) can be applied as developing solvents. As eluting agent preferably an aliphatic ether, such as diethyl ether, or an aliphatic ketone, such as acetone, is applied.

If desired, the compounds of the formulae (Ia) and (Ib) can be converted into their pharmaceutically acceptable acid addition salts. In the salt formation e.g. the following acids can be used: mineral acids, such as hydrogen halides (e.g. hydrochloric acid, hydrobromic acid), sulfuric acid, phosphoric acid, etc., organic carboxylic acids, such as formic acid, acetic acid, propionic acid, oxalic acid, glycolic acid, maleic acid, fumaric acid, succinic acid, tartaric acid, lactic acid, benzoic acid or cinnamic acid; alkylsulfonic acids, such as methanesulfonic acid; cyclohexylsulfonic acids; aspartic acid, glutamic acid, N-acetyl-aspartic acid, N-acetyl-glutamic acid, etc.

The salt-formation is performed preferably in an inert solvent, particularly in an aliphatic alcohol, such as methanol, by dissolving the free base of the formula (Ia) or (Ib) in said solvent and adding the appropriate acid thereto until the pH of the mixture becomes slightly acidic (about 6). Thereafter the salt is separated from the reaction mixture, preferably by precipitating it with a water-immiscible organic solvent, such as diethyl ether.

If the compounds of the formulae (Ia) and (Ib) are obtained in the form of their acid addition salts, they can be treated with a base in an appropriate solvent to convert them into the free bases. In this instance the salt is dissolved in an appropriate solvent or solvent mixture, such as in aqueous acetone, and the calculated amount of the base, such as concentrated aqueous ammonia, is added to this solution.

The compounds of the formulae (Ia) and (Ib) are obtained by the process of the invention with high yields and in easily identifiable forms. The elemental analysis data of the new compounds are in good agreement with the calculated values. The positions of the characteristic I.R. bands, the values of the NMR signals and the data of mass spectra prove unambiguously that the products of the formulae (Ia) and (Ib) correspond to the expected structures.

The pharmacological examinations have shown that the compounds of the general formulae (Ia) and (Ib), wherein A is as defined above, exert significant vasodilating effects, which appear primarily in connection with the significant increase of blood flow in the cerebrum and limbs.

The pharmacological tests were performed on dogs narcotized with chloralose-urethane. The blood flow of the limbs was measured at the arteria femoralis, whereas the cerebral blood flow was measured at the arteria carotis interna and arteria vertebralis. The vascular resistances to circulation were calculated from the appropriate values of blood pressure and blood flow.

The substances to be tested were administered intravenously in dosages of 1 mg/kg. The percentage changes were calculated and averaged over the test group consisting of 6 animals. The average values are listed in Table 1, along with the respective data of apovincaminic acid ethyl ester, (reference compound) used to advantage in therapy.

Table 1

| Substance tested | 1 | 2 | 3 | 4 | 5 | 6 |
|---|---|---|---|---|---|---|
| A | −8 | +12 | 0 | −3 | +148 | −65 |
| B | −52 | −5 | +2 | −7 | +140 | −65 |
| C | −25 | +35 | +78 | −54 | +93 | −61 |
| D | −18 | +27 | +41 | −43 | +120 | −54 |
| Ref. | −28 | +14 | +16 | −20 | +58 | −35 |

Notes to Table 1:
1: blood pressure
2: pulse rate
3: cerebral blood flow
4: cerebral vascular resistance
5: blood flow in the limbs
6: vascular resistance in the limbs
A: 1-(X2-methoxycarbonyl-ethylX)-1,2,3,4,6,7,12,12b-octahydro-indolo[2,3-a]quinolizine
B: 1,1-di-(X2-methoxycarbonyl-ethylX)-1,2,3,4,6,7,12,12b-octahydro-indolo[2,3-a]quinolizine
C: 1-(X2-ethoxycarbonyl-ethylX)-1,2,3,4,6,7,12,12b-octahydro-indolo[2,3-a]quinolizine
D: 1-(X2-cyano-ethylX)-1,2,3,4,6,7,12,12b-octahydro-indolo-[2,3-a]quinolizine
Ret.: apovincaminic acid ethyl ester(Xreference substance X)

The data of Table 1 clearly indicate that compounds A and B markedly increase the blood flow of the limbs; in this respect they are about 2.5 times more active than the reference substance. Compounds C and D significantly increase the cerebral blood flow; they are 2.5 times and, resp., 5 times more active than the reference substance.

The prospective dosages of the new compounds according to the invention, when administered enterally in human therapy, may range from some tenth mg/kg to 1 mg/kg. Of course, the actual dosage is selected always on the basis of the requirements of the patient and the experiences of the physician, by taking into account the relevant factors of the disorder to be treated. It should be stressed that the above dosage range is only informative in nature and cannot be interpreted as a limitation of the scope of the invention.

The compounds of the formulae (Ia) and (Ib) can be converted into pharmaceutical compositions by admixing them with non-toxic, inert, solid or liquid pharmaceutical carriers and/or diluents usable in the preparation of enteral or parenteral compositions. As carrier or diluent e.g. water, gelatine, lactose, starch, pectine, magnesium stearate, stearic acid, talc, vegetable oils (such as sunflower oil, olive oil, peanut oil, etc.), gum arabic, polyalkylene glycols, vaseline, etc. can be used. The pharmaceutical compositions may be e.g. solid compositions (such as round or edged tablets, dragees, capsules, pills, suppositories, etc.) or liquid compositions (such as oily or aqueous solutions, suspensions, emulsions, syrups, soft gelatine capsules, injectable oily or aqueous solutions or suspensions, etc.). The amount of solid carrier may vary within wide limits; a dosage unit contains preferably about 25 mg to 1 g of solid carrier. If desired or necessary, the compositions may also contain conventional pharmaceutical auxiliary agents, such as preservatives, stabilizing agents, wetting agents, emulsifying agents, salts for adjusting the osmotic pressure, buffers, flavouring agents, odouring agents, etc. The compositions may contain more than one compound of the invention and optionally also other pharmaceutically valuable substances. The compositions are prepared preferably in the form of unit dosages corresponding to the desired manner of administration. The pharmaceutical compositions can be prepared by methods known in the art, such as sieveing, mixing, granulating, pressing, dissolving, etc. If desired, the compositions can be subjected to further conventional pharmaceutical operations (e.g. sterilization).

The invention is elucidated in detail by the aid of the following non-limiting Examples.

EXAMPLE 1

Mixture of 1-(2-methoxycarbonyl-ethyl-2,3,4,6,7,12-hexahydro-1H-indolo[2,3-a]quinolizinium-perchlorate and 1,1-di-(2-methoxycarbonyl-ethyl)-2,3,4,6,7,12-hexahydro-1H-indolo-[2,3-a]quinolizinium-perchlorate 2.24 g (10.0 mmoles) of 2,3,4,6,7,12-hexahydroindolo[2,3-a]quinolizine are dissolved in 100 ml of dichloromethane, and 0.2 ml of methanol and 2.10 g (24.4 mmoles) of methyl acrylate are added to the solution. The reaction mixture is allowed to stand at room temperature for 2 days. The solvent is evaporated in vacuo and the residue is triturated with petroleum ether in order to remove the excess of methyl acrylate. The solid residue is dissolved in 15 ml of methanol, the solution is acidified to pH 6 with 70% perchloric acid, the separated salt is filtered off, and washed with ether.

4.0 g of the named mixture are obtained; m.p.: 135°–160° C.

I.R. spectrum (KBr): 3200 (indole NH), 1735, 1718 (COOCH$_3$), 1630 and 1550 (C=N)cm$^{-1}$.

EXAMPLE 2

1-(2-Methoxycarbonyl-ethyl)-1,2,3,4,6,7,12,12b-octahydro-indolo[2,3-a]quinolizine and 1,1-di-(2-methoxycarbonyl-ethyl)-1,2,3,4,6,7,12,12b-octahydro-indolo[2,3-a]quinolizine 4.0 g of the mixture obtained as described in Example 1 are hydrogenated in 100 ml of methanol in the presence of 2.0 g of palladium-on-charcoal. When the hydrogen uptake ceases the catalyst is filtered off, the filtrate is evaporated to dryness, and the residue is dissolved in aqueous methanol. The solution is rendered alkaline with 5% aqueous sodium carbonate solution and extracted with dichloromethane. The dichloromethane solutions are combined, dried, filtered, and the filtrate is evaporated to dryness. The components of the resulting mixture are separated from each other by preparative layer chromatography (adsorbent: silica gel Merck PF$_{254+366}$, developing solvent: 14:2 mixture of benzene and methanol, eluting agent: acetone). The R$_f$ value of the 1,1-disubstituted compound is greater than that of the 1-monosubstituted derivative.

1.6 g (40%) of 1,1-di-(2-methoxycarbonyl-ethyl)-1,2,3,4,6,7,12,12b-octahydro-indolo[2,3-a]quinolizine are obtained; m.p.: 226° C. (recrystallized from methanol).

I.R. spectrum (KBr): 3300 (NH), 2790, 2740 (Bohlmann bands), 1732, 1720 (COOCH$_3$)cm$^{-1}$.

Mass spectrum m)e %: 398(16,M); 397(11); 383(1); 339(2); 325(100); 311(4); 237(15); 197(50); 185(35); 170(50); 169(75).

NMR-spectrum (CDCl$_3$): δ=9.00 (1H, s, indole NH), 7.30 (4H, m, aromatic protons), 3.80 (3H, s, COOCH$_3$), 3.56 (3H, s, COOCH$_3$) ppm.

In the separation process 0.8 g (25%) of 1-(2-methoxycarbonyl-ethyl)-1,2,3,4,6,7,12,12b-octahydro-indolo[2,3,-a]-quinolizine are obtained. The hydrochloride of the product melts at 245° C. under decomposition.

I.R. spectrum (KBr): 2780 (Bohlmann band), 1725 (COOCH$_3$)cm$^{-1}$.

Mass spectrum m(e (%): 312(90,M); 311(100); 297(3); 281(10); 253(2); 239(70); 225(10); 197(40); 170(22); 169(23).

EXAMPLE 3

1-(2-Ethoxycarbonyl-ethyl)-2,3,4,6,7,12-hexahydro-1H-indolo[2,3-a]quinolizinium-perchlorate 10.1 g (45 mmoles) of 2,3,4,6,7,12-hexahydroindolo[2,3-a]quinolizine are dissolved in 230 ml of dichloromethane, 4.5 ml of ethanol and 5.1 g (50 mmoles) of ethyl acrylate are added to the solution, and the reaction mixture is allowed to stand at room temperature for 2 days. The solvent is evaporated in vacuo, the residue is admixed with 70 ml of ethanol, and the solution is acidified to pH 6 with 70% perchloric acid. The separated substance is filtered off and washed with ethanol and ether.

12.5 g (65%) of the title compound are obtained; m.p.: 166° C.

I.R. spectrum (KBr): 3240 (indole NH), 1725 (COOC$_2$H$_5$), 1630, 1550 (C=N)cm$^{-1}$.

EXAMPLE 4

1-(2-Ethoxycarbonyl-ethyl)-1,2,3,4,6,7,12,12b-octahydro-indolo[2,3-a]quinolizine hydrochloride 6.0 g (14 mmoles) of the product of Example 3 are dissolved in a mixture of 90 ml of ethanol and 30 ml of dichloromethane, and the mixture is hydrogenated in the presence of 10 g of palladium-on-charcoal. After the uptake of the calculated amount of hydrogen (about 1 hour) the catalyst is filtered off and the filtrate is evaporated in vacuo. The residue is admixed with 50 ml of water, the mixture is rendered alkaline with 5% aqueous sodium carbonate solution, and the alkaline mixture is extracted with dichloromethane. The organic phase is dried over magnesium sulfate, filtered and evaporated. The oily residue is dissolved in 20 ml of ethanol, the solution is acidified to pH 6 with ethanolic hydrochloric acid, the separated substance is filtered off, and washed with a small amount of alcohol and ether.

3.4 g (68%) of the title compound are obtained; m.p.: 244° C. (after recrystallization from ethanol).

I.R. spectrum (Kbr): 3145 (indole NH), 2790, 2730 (Bohlmann bands), 1724 (COOC$_2$H$_5$)cm$^{-1}$.

NMR spectrum (CDCl$_3$): $\delta$=8.80 (1H, s, indole NH), 7.30 (4H, m, aromatic protons), 4.18 (2H, q, COOCH$_2$CH$_3$), 1.25 (3H, t, COOCH$_2$C$\underline{H}$$_3$) ppm.

Mass spectrum m/e (%): 32$_6$(85,M); 325(95); 296(17); 281(18); 253(3); 239(100); 225(14); 197(40); 185(13); 170(35); 169(35).

EXAMPLE 5

1-(2-Ethoxycarbonyl-ethyl)-2,3,4,6,7,12-hexahydro-1H-indolo[2,3-a]quinolizine 2.2 g (10 mmoles) of 2,3,4,6,7,12-hexahydro-indolo[2,3-a]quinolizine are dissolved in 100 ml of dichloromethane, 0.5 ml of ethanol and 2.3 g (25 mmoles) of ethyl acrylate are added to the solution, and the mixture is allowed to stand at room temperature for 2 days under argon atmosphere. The solvent is evaporated in vacuo, the residue is triturated with 3×3 ml of petroleum ether, the liquid is decanted, and the solid is dried.

2.75 g (86%) of the title compound are obtained; m.p.: 72°–74° C.

EXAMPLE 6

1-(2-Ethoxycarbonyl-ethyl)-1,2,3,4,6,7,12,12b-octahydro-indolo[2,3-a]quinolizine hydrochloride 2.5 g (7.7 mmoles) of the product of Example 5 are dissolved in 150 ml of ethanol, and the solution is hydrogenated in the presence of 2 g of palladium-on-charcoal. After the uptake of the calculated amount of hydrogen (about 30 minutes) the catalyst is filtered off, and the solvent is evaporated in vacuo. The residue is dissolved in 10 ml of ethanol, the pH of the solution is adjusted to 5 with methanolic hydrochloric acid, the separated precipitate is filtered off, washed with ethanol and ether, and dried.

1.2 g (50%) of the title compound are obtained. The physical constants of the product are identical with those of the compound prepared according to Example 4.

EXAMPLE 7

1-(2-Ethoxycarbonyl-ethyl)-1,2,3,4,6,7,12,12b-octahydro-indolo[2,3-a]quinolizine hydrochloride 0.35 g (1 mmole) of 1-(2-methoxycarbonyl-ethyl)-1,2,3,4,6,7,12,12b-octahydro-indolo[2,3-a]quinolizine hydrochloride are partitioned between 10 ml of dichloromethane and 3 ml of 5% aqueous sodium carbonate solution, and the aqueous phase is extracted with 2×3 ml of dichloromethane. The organic phases are combined, dried over magnesium sulfate, filtered, and the filtrate is evaporated. The oily residue is dissolved in 15 ml of absolute ethanol, 50 mg of sodium ethoxide are added to the solution, and the mixture is boiled for 2 hours. Thereafter the mixture is cooled, the sodium ethoxide is decomposed with glacial acetic acid, and the solution is evaporated to dryness in vacuo. The residue is admixed with 10 ml of 5% aqueous sodium carbonate solution, and the mixture is extracted with 20 ml of dichloromethane. The organic phase is filtered, the filtrate is dried over magnesium sulfate, filtered again, and then evaporated in vacuo to dryness. The obtained 0.30 g of oily residue are dissolved in 2 ml of ethanol, the solution is acidified to pH 6 with ethanolic hydrochloric acid, the separated salt is filtered off, washed with ethanol and ether, and dried.

0.25 g (78%) of the title compound are obtained; m.p.: 244° C.

EXAMPLE 8

1-(2-Cyano-ethyl)-2,3,4,6,7,12-hexahydro-1H-indolo[2,3-a]quinolizinium-perchlorate 2.24 g (10 mmoles) of 2,3,4,6,7,12-hexahydroindolo[2,3-a]quinolizine are dissolved in 100 ml of dichloromethane, 1.25 g (23 mmoles) of acrylonitrile are added to the solution, and the reaction mixture is allowed to stand at room temperature for 2 days. The solvent is evaporated in vacuo, the residue is dissolved in 20 ml of methanol, and the solution is acidified to pH 6 with 70% perchloric acid. The separated crystalline substance is filtered off and washed with ether.

3.2 g (86%) of the title compound are obtained; m.p.: 210° C. (decomposition).

I.R. spectrum (KBr): 3280 (indole NH), 2280 (CN), 1625, 1550 (C=N)cm$^{-1}$.

EXAMPLE 9

1-(2-Cyano-ethyl)-1,2,3,4,6,7,12,12b-octahydro-indolo[2,3-a]quinolizine hydrochloride 2.50 g (6.6 mmoles) of the product of Example 8 are hydrogenated in 120 ml of methanol in the presence of 2.0 g of palladium-on-charcoal. After the uptake of the calculated amount of hydrogen (about 25 minutes) the catalyst is filtered off and the filtrate is evaporated in vacuo. The residue is admixed with 30 ml of water, the mixture is rendered alkaline with aqueous sodium carbonate solution, and extracted with dichloromethane. The dichloromethane solutions are combined, dried, filtered, and the filtrate is evaporated. The oily residue is dissolved in 10 ml of methanol, and the solution is acidified to pH 6 with methanolic hydrochloric acid. The separated substance is filtered off, washed with ether and dried.

1.5 g (72%) of the title compound are obtained; m.p.: 178° C. (decomposition).

I.R. spectrum (KBr): 1610 (aromatic vibration), 2235 (CN)cm$^{-1}$.

Mass spectrum m(e (%): 279(45,M); 272(38); 239(100); 197(14); 170(11); 169(13).

EXAMPLE 10

Tablets containing 1-(2-ethoxycarbonyl-ethyl-1,2,3,4,6,7,12,12b-octahydro-indolo[2,3-a]quinolizine hydrochloride Composition of one tablet:

| | |
|---|---|
| 1-(X2-ethoxycarbonyl-ethylX)-1,2,3,4,6,7,12,12b-octahydro-indolo[2,3-a]quinolizine hydrochloride (Xactive principleX) | 5 mg |
| gelatine | 3 mg |
| magnesium stearate | 2 mg |
| talc | 5 mg |
| potato starch | 40 mg |
| lactose | 95 mg |

The active principle is admixed with the lactose and 75% of the potato starch. The resulting homogeneous mixture is kneaded with an aqueous solution of the gelatine, the wet mass is granulated, and the granules are dried. The granules are admixed with the talc, the magnesium stearate and the remaining 25% of the potato starch, and the mixture is compressed into tablets. If desired, the tablet can be provided with a dividing line in order to facilitate dosage.

What we claim is:
1. 1,1-Di-(2-methoxycarbonyl-ethyl)-1,2,3,4,6,7,12,12b-octahydro-indolo[2,3-a]quinolizine or the hydrochloride thereof.
2. A vasodilating composition which consists essentially of a vasodilatory effective amount of the compound defined in claim 1 in a pharmaceutically effective carrier.